(12) United States Patent
Rakic et al.

(10) Patent No.: US 10,180,397 B2
(45) Date of Patent: Jan. 15, 2019

(54) LASER SYSTEM FOR IMAGING AND MATERIALS ANALYSIS

(71) Applicants: THE UNIVERSITY OF QUEENSLAND, St. Lucia, Queensland (AU); UNIVERSITY OF LEEDS, St. Lucia, Queensland (AU)

(72) Inventors: Aleksandar D. Rakic, Chapel Hill (AU); Paul Dean, West Yorkshire (GB); Alexander Giles Davies, West Yorkshire (GB); Dragan Indjin, West Yorkshire (GB); Edmund Harold Linfield, West Yorkshire (GB); Stephen James Wilson, Camp Hill (AU); Thomas Taimre, Pullenvale (AU); Karl Bertling, Bridgeman Downs (AU); Yah Leng Lim, Chapel Hill (AU)

(73) Assignees: The University of Queensland, St. Lucia (AU); University of Leeds, St. Lucia (AU)

( * ) Notice: Subject to any disclaimer, the term of this patent is extended or adjusted under 35 U.S.C. 154(b) by 26 days.

(21) Appl. No.: 14/913,507

(22) PCT Filed: Aug. 22, 2014

(86) PCT No.: PCT/AU2014/000828
§ 371 (c)(1),
(2) Date: Feb. 22, 2016

(87) PCT Pub. No.: WO2015/024058
PCT Pub. Date: Feb. 26, 2015

(65) Prior Publication Data
US 2016/0202180 A1   Jul. 14, 2016

(30) Foreign Application Priority Data
Aug. 22, 2013 (AU) ................... 2013903171

(51) Int. Cl.
*G01J 3/42* (2006.01)
*G01N 21/45* (2006.01)
*G01N 21/3581* (2014.01)

(52) U.S. Cl.
CPC .............. *G01N 21/45* (2013.01); *G01J 3/42* (2013.01); *G01N 21/3581* (2013.01); *G01N 2201/0612* (2013.01); *G01N 2201/12* (2013.01)

(58) Field of Classification Search
CPC .................................................. G01N 21/45
See application file for complete search history.

(56) References Cited

U.S. PATENT DOCUMENTS

| 2,552,184 A | * | 5/1951 | Koch | ............. G02B 5/282 313/112 |
| 4,905,170 A | * | 2/1990 | Forouhi | ............. G01N 21/17 356/631 |

(Continued)

FOREIGN PATENT DOCUMENTS

| CN | 101055224 A | 10/2007 |
| CN | 101341421 A | 1/2009 |

(Continued)

OTHER PUBLICATIONS

Valavanis et al., "Self-Mixing Interferometry With Terahertz Quantum Cascade Lasers", Jan. 2013, IEEE Sensors Journal, vol. 13, No. 1, pp. 37-43.*

(Continued)

*Primary Examiner* — David P Porta
*Assistant Examiner* — Jeremy S Valentiner
(74) *Attorney, Agent, or Firm* — Nixon & Vanderhye P.C.

(57) ABSTRACT

A THz quantum cascade laser is used to investigate a target by directing a first beam of laser radiation from the laser at the target to thereby produce a second beam of laser radia- (Continued)

tion by interaction of the first beam with the target. Self-mixing of the first and second beams occurs within the laser and causes variations in a signal such as the operating voltage of the laser. An operating parameter of the laser that affects the interaction of the first beam with, the target is varied. The operating voltage is monitored and processed to determine phase and amplitude changes associated with material properties of the target. Consequently in one embodiment the invention provides for processing the variations in the signal to produce various images of the target.

25 Claims, 13 Drawing Sheets

(56) References Cited

U.S. PATENT DOCUMENTS

| | | | | |
|---|---|---|---|---|
| 5,916,717 | A * | 6/1999 | Yang | G03F 7/162 430/30 |
| 7,920,249 | B2 | 4/2011 | Heinks et al. | |
| 2004/0195511 | A1 * | 10/2004 | Elmore | G01J 3/02 250/339.02 |
| 2012/0176595 | A1 | 7/2012 | Van Der Lee et al. | |

FOREIGN PATENT DOCUMENTS

| | | |
|---|---|---|
| CN | 102089617 A | 6/2011 |
| CN | 102331313 A | 1/2012 |
| CN | 102549449 A | 7/2012 |
| CN | 102792183 A | 11/2012 |
| CN | 102998281 A | 3/2013 |
| CN | 103018747 A | 4/2013 |
| EP | 2 520 924 A1 | 11/2012 |
| JP | 2012-132740 A | 7/2012 |
| JP | 2013-142654 A | 7/2013 |

OTHER PUBLICATIONS

Rakić et al., Swept-frequency feedback interferometry using terahertz frequency QCLs: a method for imaging and materials analysis, Sep. 23, 2013, Optics Express, vol. 21, Iss. 19, pp. 22194-22205 (Year: 2013).*
Examination Report 1: Chinese Examiner's Objections to Chinese Patent Application No. 201480056750.9 dated Feb. 28, 2017, and English translation.
Extended European Search Report dated Mar. 30, 2017, issued in European Patent Application No. 14837261.8.
Dean, Paul, et al., "Terahertz imaging through self-mixing in a quantum cascade laser," Optics Letters, Jul. 1, 2011, vol. 36, No. 13, pp. 2587-2589, XP-001564049.
Fathi, M. T., et al., "Simultaneous measurement of thickness and refractive index by a single-channel self-mixing interferometer," IET Optoelectronics, 2012, vol. 6, Iss. 1, pp. 7-12.
International Search Report for PCT/AU2014/000828 dated Nov. 21, 2014, 4 pages.
Written Opinion of the ISA for PCT/AU2014/000828 dated Nov. 21, 2014, 4 pages.
Valvanis et al., "Self-Mixing Interferometry With Terahertz Quantum Cascade Lasers", *IEEE Sensors Journal* (2013), vol. 13, No. 1, published Sep. 12, 2012, pp. 37-43.

* cited by examiner

LASER SYSTEM FOR IMAGING AND MATERIALS ANALYSIS

This application is the U.S. national phase of International Application No. PCT/AU2014/000828 filed 22 Aug. 2014 which designated the U.S. and claims priority to AU Patent Application No. 2013903171 filed 22 Aug. 2013, the entire contents of each of which are hereby incorporated by reference.

TECHNICAL FIELD

The present invention is concerned with a laser based method and system for materials analysis and imaging.

BACKGROUND

Any references to methods, apparatus or documents of the prior art are not to be taken as constituting any evidence or admission that they formed, or form part of the common general knowledge.

Significant scientific effort has been invested in the realization of imaging and materials analysis systems over the past two decades. One outcome of this effort is that THz time-domain spectroscopy (TDS) has established itself as a significant tool for coherently probing solid-state, liquid, and gaseous systems at THz frequencies. Key to the success of THz TDS is its capability of measuring complex refractive indices of samples over bandwidths as large as 100 THz, due to its intrinsic ability to resolve the electric field amplitude of broadband THz pulses coherently and with subpicosecond resolution, as well as its insensitivity to thermal background radiation. However, THz TDS systems in general have signal-to-noise ratios (SNRs) that are practically useful only below ~3 THz. Furthermore, their spectral resolution is typically limited to no better than ~5 GHz (worse in high-bandwidth systems), and they are restricted to low THz powers on the order of 10-100 µW for commonly used optically-pumped photoconductive emitters.

Moreover, spectroscopic data acquisition is slow and the technique relies on bulky and expensive ultrafast laser sources for the generation and coherent detection of THz radiation.

Recently the THz quantum cascade laser (QCL) has emerged as the established laboratory source of high-power radiation in the frequency range ~1-5 THz. THz QCLs have been shown to exhibit remarkable spectral purity with quantum-limited linewidths, making them ideally-suited to coherent THz systems. Nevertheless, owing to the challenges of coherently detecting the emission from such sources, most system developments have focussed on incoherent approaches to imaging and materials analysis. Coherent detection schemes have, however, permitted the phase and/or frequency of the THz field to be resolved. By exploiting the heterodyne mixing between a free-running QCL and a local oscillator derived from a gas laser, high-resolution frequency-resolved gas spectroscopy has been reported. Phase-sensitive detection using a heterodyne approach has also enabled coherent inverse synthetic aperture radar imaging. However, heterodyne systems generally suffer from the disadvantage that they are complex and bulky.

It is an object of the invention to provide a laser based imaging or remote materials sensing system that is an improvement, or at least a useful alternative, to the aforementioned systems of the prior art.

SUMMARY OF THE INVENTION

According to a first aspect of the present invention there is provided a method for investigating a target comprising the steps of:
  directing a first beam of radiation from a laser at the target to thereby produce a second beam of laser radiation by interaction of the first beam with the target wherein self-mixing of the first and second beams occurs within the laser,
  varying a parameter affecting the interaction of the first beam with the target;
  detecting a signal arising from the self-mixing; and
  processing the signal to thereby determine phase and amplitude changes associated with material properties of the target.

Preferably the laser comprises a quantum cascade laser (QCL).

Alternatively, the laser may comprise any one of:
  an interband quantum cascade (ICL) laser; or
  a Helium Neon gas laser; or
  a Carbon Dioxide laser; or
  an optically pumped fiber laser.

Preferably the laser is arranged to operate in the terahertz (THz) band. Alternatively, it may be arranged to operate in another frequency band such as the infrared band.

Preferably the step of detecting the signal involves measuring an electrical signal across terminals of the laser.

Preferably the step of varying a parameter of the first beam of laser radiation includes applying a modulation to a current for driving the laser.

Preferably the modulation comprises a continuous wave frequency modulation of the laser beam frequency. For example, in the preferred embodiment of the invention the modulation comprises superimposing a modulating sawtooth current signal onto a dc current supply for the semiconductor laser.

In a preferred embodiment of the invention the step of processing the signal includes detecting a first type of change of a waveform of the signal associated with a phase shift imparted by the interaction of the first beam with the target. For example the first type of change of the waveform may comprise a phase shift of the waveform.

Preferably the step of processing the signal further includes detecting a second type of change of the waveform of the signal associated with an attenuation imparted by the interaction of the first beam with the target. For example the second type of change may comprise a narrowing or widening of a peak of the waveform or a change in the amplitude of the waveform In an alternative embodiment of the present invention the step of varying the parameter may comprise moving the target longitudinally relative to a source of the first beam of laser radiation.

The method may include processing the signal to thereby determine phase and amplitude changes associated with material properties of the target to derive a refractive index (n) and an extinction coefficient (k) of the target.

Where the method includes processing the signal to determine the refractive index (n) and extinction coefficient (k) of the target the method will preferably further involve causing the first beam of laser radiation to interact with a portion of the target having known properties.

Preferably the method includes fitting a mathematical model of the laser self-mixing to data for each of a number of positions of the target to obtain a set of parameter values for each of the positions.

The method may include applying known values of n and k of two materials from said portion of the target to thereby derive n and k of a third material of the target, being a material under test.

The method may include mechanically scanning the target by moving the target relative to the laser to thereby sense variations in the properties of the target as a function of location thereof.

The method may include processing the sensed variations in the properties of the target to produce an image of the target.

In a preferred embodiment of the invention the method includes measuring variations in the signal at each of a number of positions during the mechanical scanning.

Preferably the method includes removing the effect of power modulation of the laser from each of said measurements. For example, the step of removing the effect of power modulation may comprise subtracting a reference slope from measurements made at each of the positions.

In a preferred embodiment of the invention the measurements are taken to avoid the effect of transients at the edges of the modulation period of the laser.

For example, the method may include processing only a central portion of each period of the signal at each scanning position.

In a preferred embodiment of the invention the method includes determining a reflection coefficient of the target at each position.

The step of determining the reflection coefficient may be based on the integral of the absolute value of the signal over time.

The method may include producing an image from the target by fitting time domain traces of the signal to a mathematical model of the laser feedback self-mixing to thereby calculate variations in a feedback parameter of the model wherein the image is generated by plotting the feedback parameter for each of a number of the positions.

According to a further embodiment of the present invention there is provided a system for investigating a target comprising:
  a laser;
  a target assembly arranged to return a beam from the laser to the laser after interaction with a target of said assembly;
  a data acquisition assembly responsive to electrical terminals of the laser; and
  a computational device responsive to the data acquisition assembly, wherein the computational device is programmed to determine phase and amplitude changes associated with the target and imparted on to the beam by interaction therewith.

Preferably the laser is under control of the computational device for operation of the laser and variation of its operating parameters.

Preferably the system further includes a translation assembly arranged to impart a relative motion between the laser and the target.

In a preferred embodiment of the invention the translation assembly includes one or more actuators under control of the computational device wherein the computational device is programmed to operate the translation assembly for data acquisition at each of a number of positions of the target.

According to a further aspect of the present invention there is provided a computer software product comprising a media, for example an optical, magnetic or solid state data storage device, bearing tangible machine readable instructions for an electronic processor to:

operate a laser to direct a laser beam at a target assembly;
acquire electrical data being a function of self-mixing of the laser beam with a reflection thereof from the target assembly; and
determine phase and amplitude changing properties of a target portion of the target assembly on the basis of the acquired electrical data.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

In FIG. 2D, flat mirror 42b is used instead of parabolic reflector 42 in FIG. 2C.

DETAILED DESCRIPTION OF PREFERRED EMBODIMENTS

A preferred embodiment of the present invention comprises a method for coherent imaging and materials analysis using a THz QCL feedback interferometer 2 in reflection mode. At the heart of this scheme is the realization that a portion of the emitted THz radiation, returning from an external target 10, when re-injected into the laser cavity 5, yields information about both amplitude and phase change properties of the remote target that are discernible through changes in laser operating parameters. Using this scheme, the inventors concurrently obtain two-dimensional amplitude-like and phase-like images with minimal signal processing, which are indicative of the refractive index distribution and variation in absorption respectively. The inventors demonstrate that this coherent detection method enables extraction of the refractive index and absorption coefficient of materials under test. Key to a preferred embodiment of the invention is the implementation of a THz swept-frequency delayed self-homodyning ('self-mixing') scheme that enables phase-sensitive detection of the THz field emitted by a QCL source. As well as phase-stability, the use of a QCL as the THz source affords the benefit of high output power spectral density, several orders of magnitude better spectral resolution than TDS, and the potential for high-speed measurements.

Figure 1A:
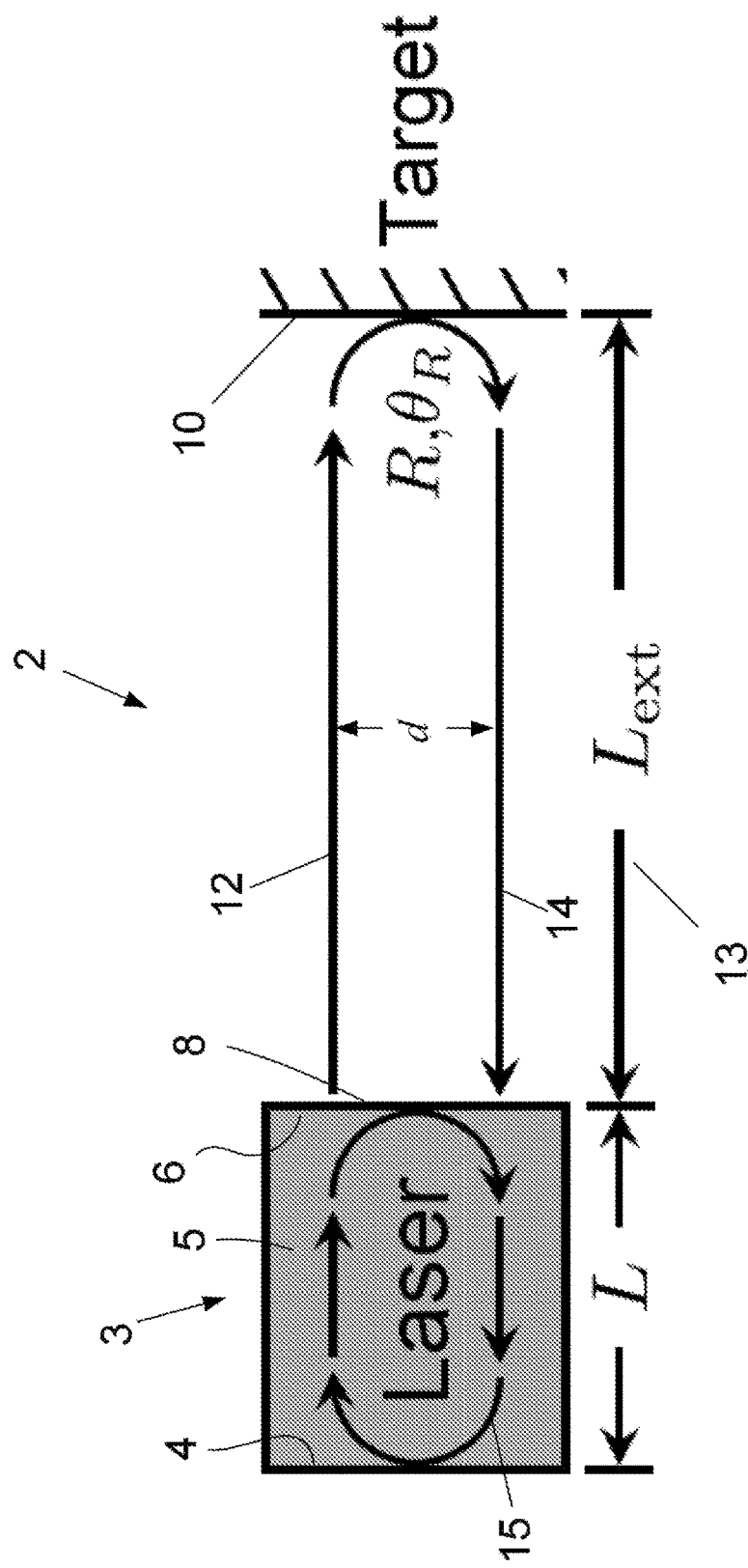
FIG. 1A is a schematic diagram showing an intensity, and frequency modulated, self-mixing laser interferometer according to a preferred embodiment of the present invention.

The basic structure and operating principles of a self-mixing interferometer according to a preferred embodiment of the present invention are shown in FIG. 1a. The re-injected light interferes ('self-mixes') with the intra-cavity electric field, causing small variations in the fundamental laser parameters including the threshold gain, emitted power, lasing spectrum, and laser terminal voltage.

The interferometer includes a laser 3 which may for example, and without limitation, be a Quantum Cascade Laser (QCL), an Interband Cascade Laser (ICL), a Helium Neon laser a Carbon Dioxide laser or an optically pumped fiber laser. As will be understood from the subsequent discussion of preferred embodiments of the invention, other types of laser may also be used provided that they have sufficiently low phase noise.

Whichever particular type of laser is used it includes a gain medium that is sandwiched between two mirrors 4, 6 and which has an exit facet 8 located an external a distance $L_{ext}$ from a target 10. In use the laser emits a first laser beam 12 which is returned to the laser from the target 10 in the form of a second returned beam 14. As the beam interacts with the target 10 (or as it is sometimes referred to herein "the sample") the target imparts phase and amplitude changes due to its material properties. Consequently the second, returned beam 14 has a phase and an amplitude that differs from that of the first laser beam 12. The second returned beam 14 interacts with the first laser beam 12 in the gain medium of the laser 3 thereby causing "self-mixing" which results in measurable variations in the operating parameters of the laser.

The above explanation emphasizes a ray model of the interaction of the emitted laser beam with the target and FIG. 1A shows the first laser beam 12 and the second returned beam 14 displaced a distance d from each other. Those skilled in the art will realize that this is a convention for explanatory purposes and that the first laser beam 12 second and the returned beam 14 are not in fact displaced but rather are collinear and that they produce a standing wave between the target and the laser.

Whilst optical feedback affects almost all laser parameters, the two that are most conveniently monitored are the emitted optical power and the voltage across the laser terminals. Of these, monitoring the laser terminal voltage is preferred as it removes the need for an external terahertz detector. The small voltage variation (referred to as the 'self-mixing signal') depends on both the amplitude and phase of the electric field of the reflected laser beam. This configuration thus creates a compact, coherent sensor that can probe information about the complex reflectivity or complex refractive index of the external target.

The homodyne (coherent) nature of a self-mixing scheme inherently provides very high sensitivity detection, potentially at the quantum noise limit, and therefore a high signal-to-noise ratio can be expected in the self-mixing signal. Furthermore, the maximum speed of response to optical feedback is determined by the frequency of relaxation oscillations in the laser itself. In the case of THz QCLs, the lifetime of the upper state of the lasing transition is limited by elastic and inelastic scattering mechanisms to a few picoseconds enabling response frequencies on the order of tens of GHz.

The inventors use a three mirror model to describe the laser system under feedback which is equivalent to the steady-state solution to the model proposed by Lang and Kobayashi. In this model, only one round-trip in the external cavity is considered. The phase shift in the external cavity is composed of the transmission phase shift arising from the optical path length as well as the phase change on reflection from the target. The reflectivity of the target together with the phase change on reflection form a complex pair which is equivalent to the complex refractive index of the target.

Figure 1B:
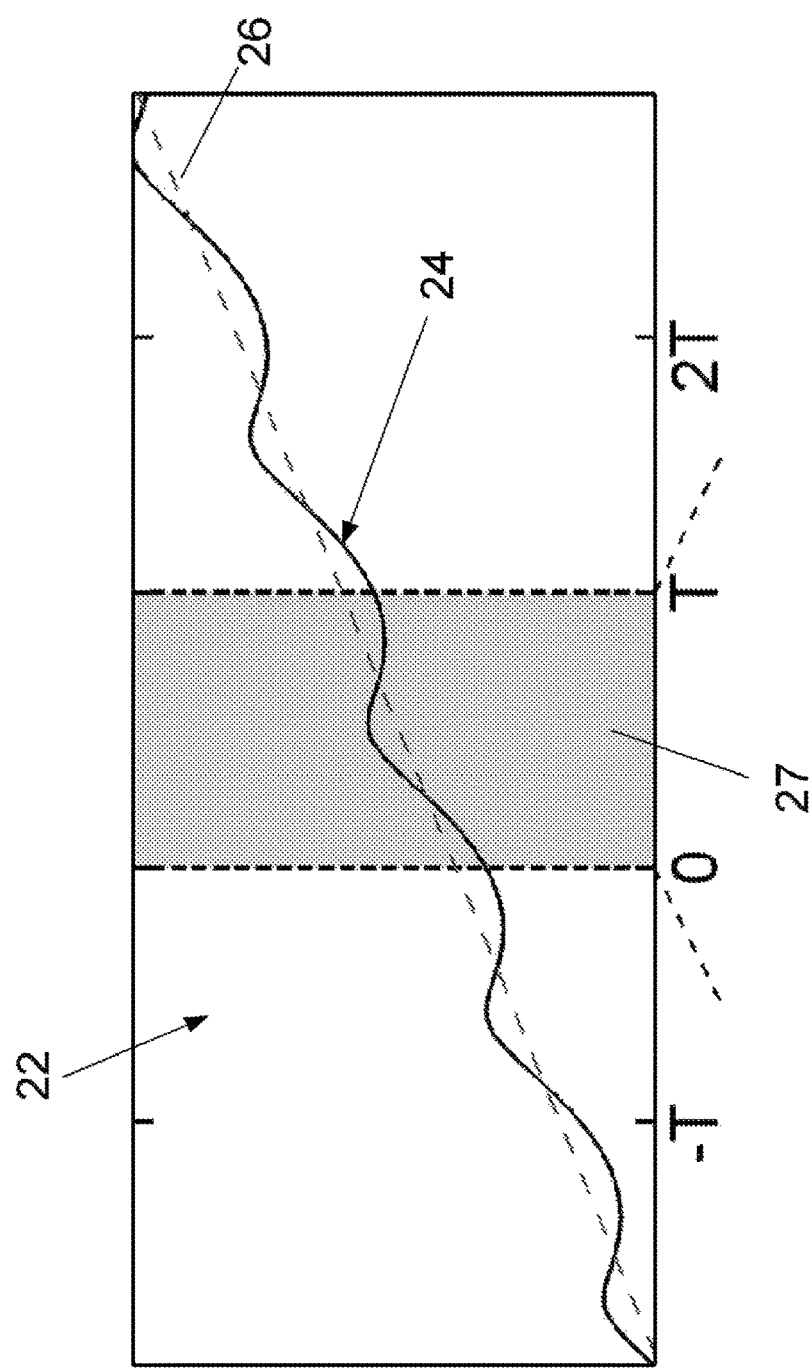
FIG. 1B is a graph of a self-mixing signal observed through variation in laser terminal voltage as a function of time wherein the broken line represents a reference slope and the solid line represents a typical voltage signal due to the self-mixing.
Figure 1C:
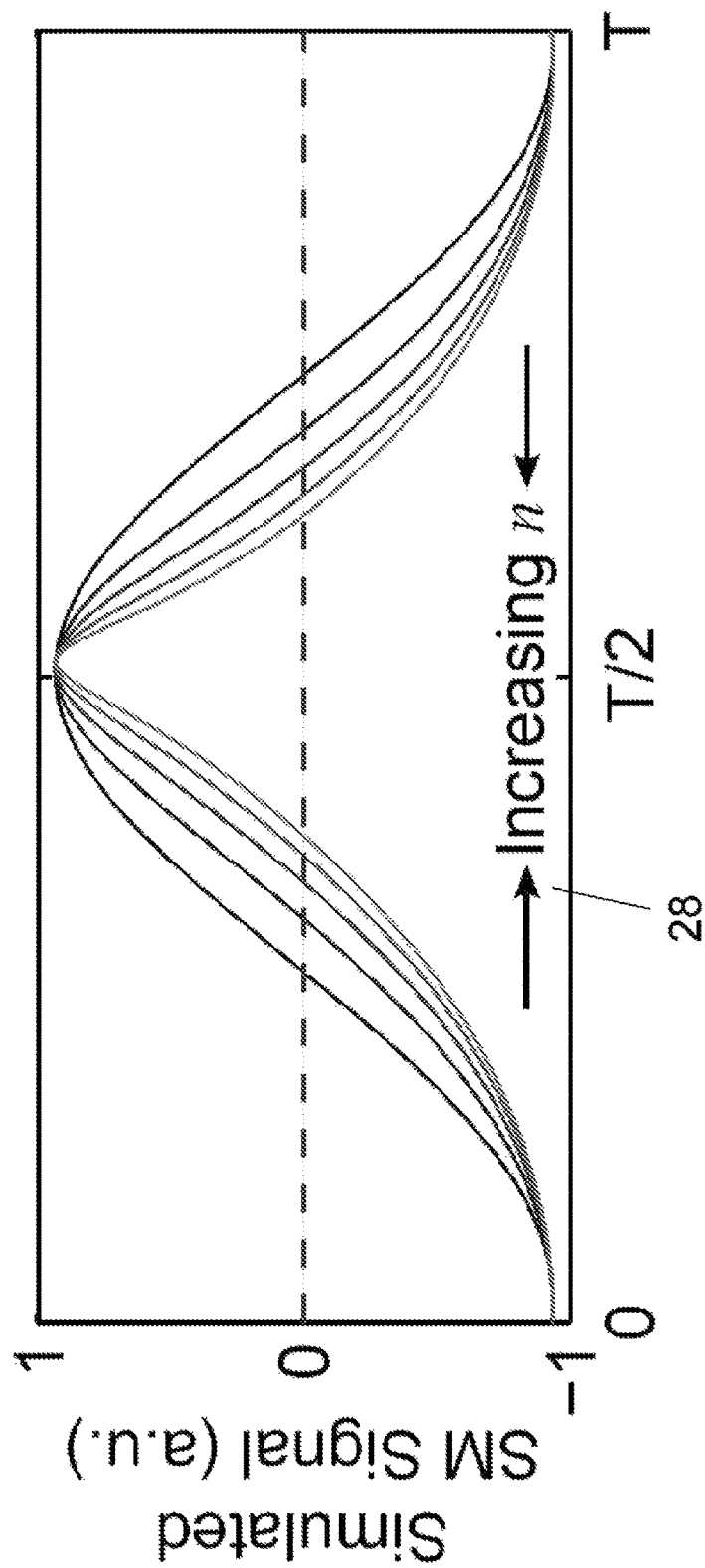
FIG. 1C is a graph of a single period T of the self-mixing signal showing the effect of increasing refractive index n of the target. The waveform narrows with increasing n, and the peak shifts to a later time.
Figure 1D:
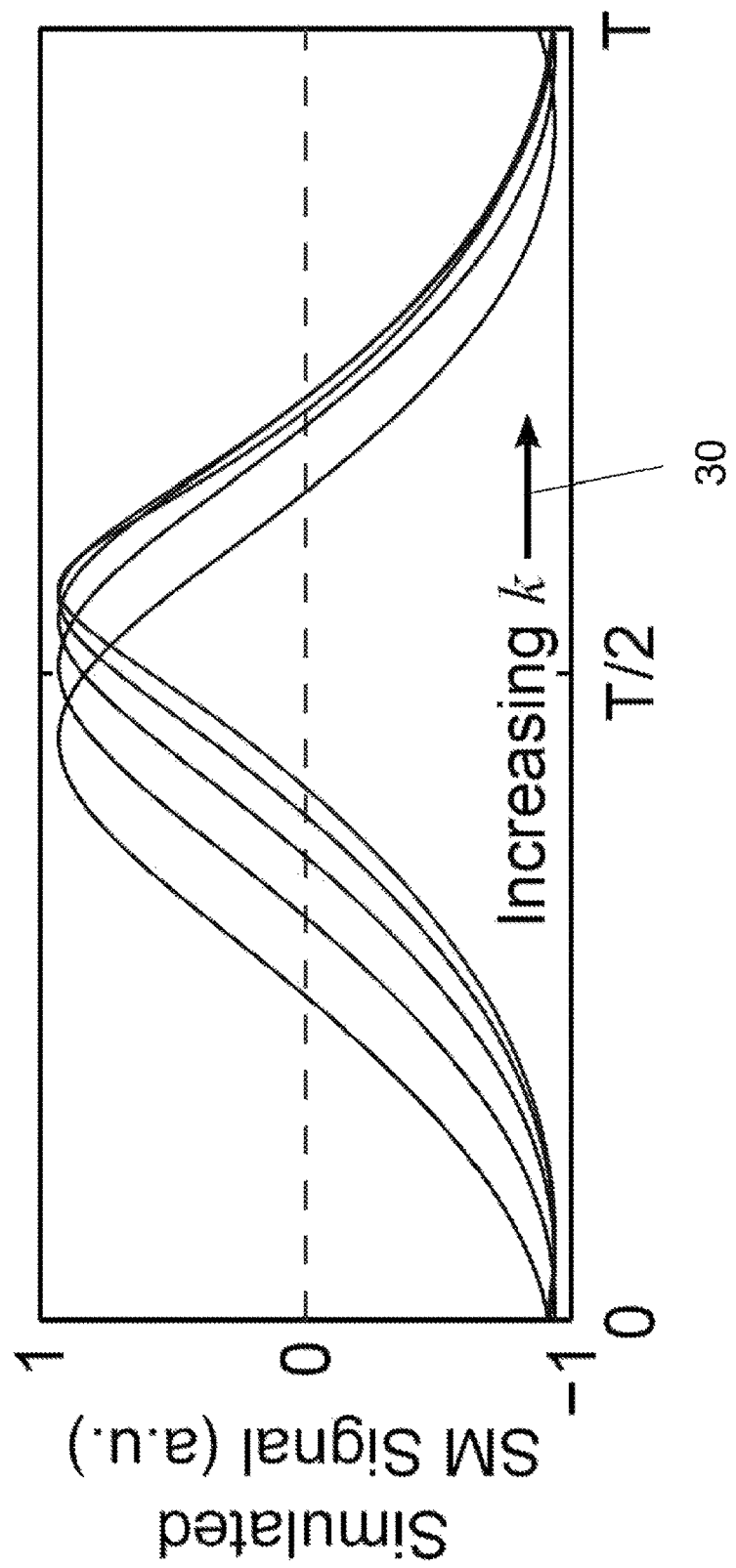
FIG. 1D is a graph of a single period T of the self-mixing signal showing the effect of increasing extinction coefficient k of the target which mainly translates the waveform to a later time.

When the external target is displaced longitudinally, the laser system is swept through a set of compound cavity resonances. The equivalent effect may be obtained by changing the laser frequency, which is accomplished in a preferred embodiment of the invention by applying a linear modulation of the laser driving current. The primary effect of this current sweep is a modulation of both the emitted laser power and the voltage developed across the laser terminals. The secondary effect, which is of most importance here, is a linear change of the lasing frequency with current (frequency chirp). This approach in essence constitutes a continuous-wave (cw) frequency-modulated system for coherently probing the remote target. During the frequency sweep, the self-mixing signal is observed as a set of periodic perturbations embedded in the modulated voltage signal 22 (see FIG. 1b). The temporal separation between the peaks of the self-mixing signal waveform 24, as well as its shape and phase, depends on the length of the external cavity and the complex reflectivity of the target. This is illustrated in FIGS. 1c and 1d which considers one period 27 (identified in FIG. 1B) of the self-mixing waveform with the linear ramp 26 removed. FIG. 1c shows the effect of increasing the real part of the complex refractive index n, leading principally to a narrowing 28 of the waveform due to stronger feedback. On the other hand, an increase in the imaginary part of the complex refractive index (extinction coefficient) k predominately produces a phase shift 30 in the waveform whilst leaving the shape of the waveform unchanged, as shown in FIG. 1d. This effect is mainly due to the strong link between k and the phase-shift on reflection.

Thus, through analysis of the shape and phase of the self-mixing waveform, the complex reflectivity of the target may be deduced. The way in which information about n and k affects the self-mixing signal is suitably described through the well-known steady-state solution to the Lang and Kobayashi model. In particular, information about the complex refractive index of the target enters the Lang and Kobayashi model through the feedback parameter C, the effective external cavity length $L_{ext}$, and the phase change on reflection R.

Embodiments of the invention are equally applicable to extracting values for n and k of a material under test, and for high-contrast imaging of spatial variation in these quantities across a target.

An example of a preferred embodiment of the invention will be described with reference to a custom-designed composite target consisting of an aluminium cylinder 1 inch in diameter with three cylindrical bores containing different plastics, namely polyoxymethylene (POM, also known as acetal), polyvinyl chloride (PVC), and nylon 6 (PA6, also known as polycaprolactam). A further target containing the plastics polycarbonate (PC), and two samples of high-density polyethylene (HDPE and HDPE Black) has also been characterised.

Figure 2A:
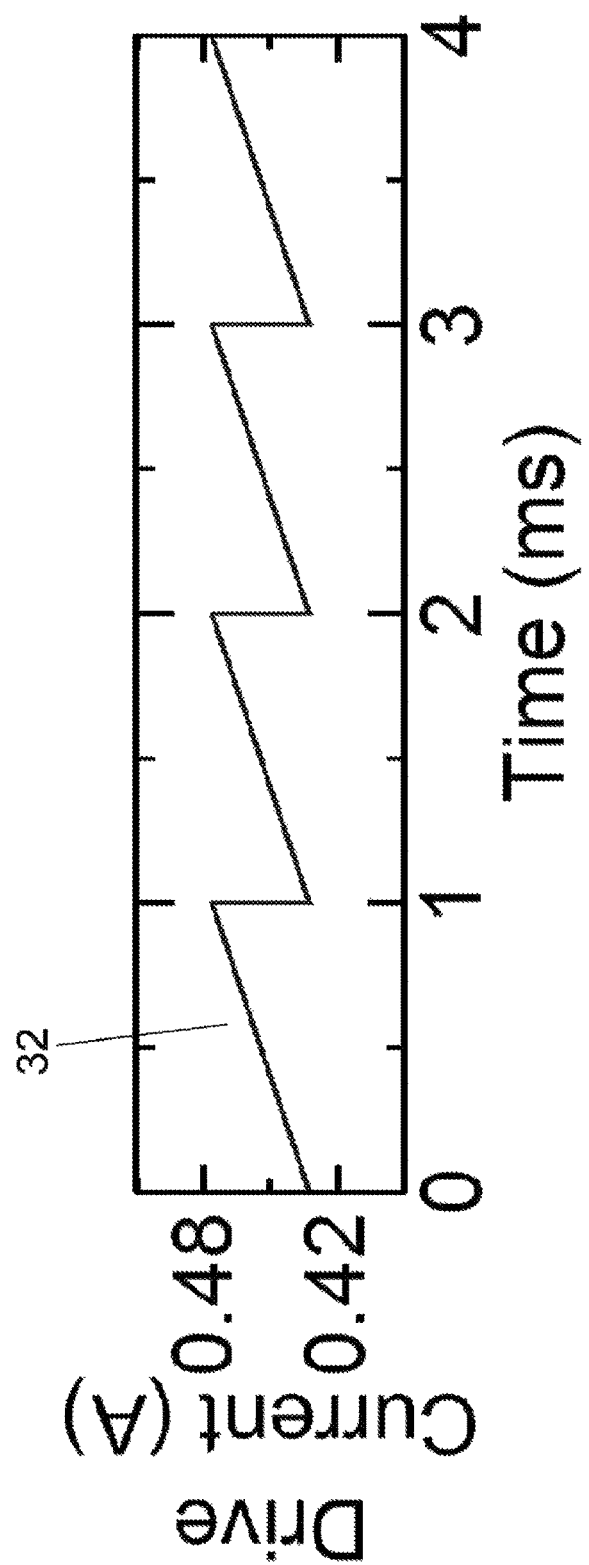
FIG. 2A is a graph of a current stimulus signal applied to the QCL of FIG. 2C. The current range was selected to sweep the laser frequency through three external cavity resonances in the region where the laser was most sensitive to optical feedback.
Figure 2B:
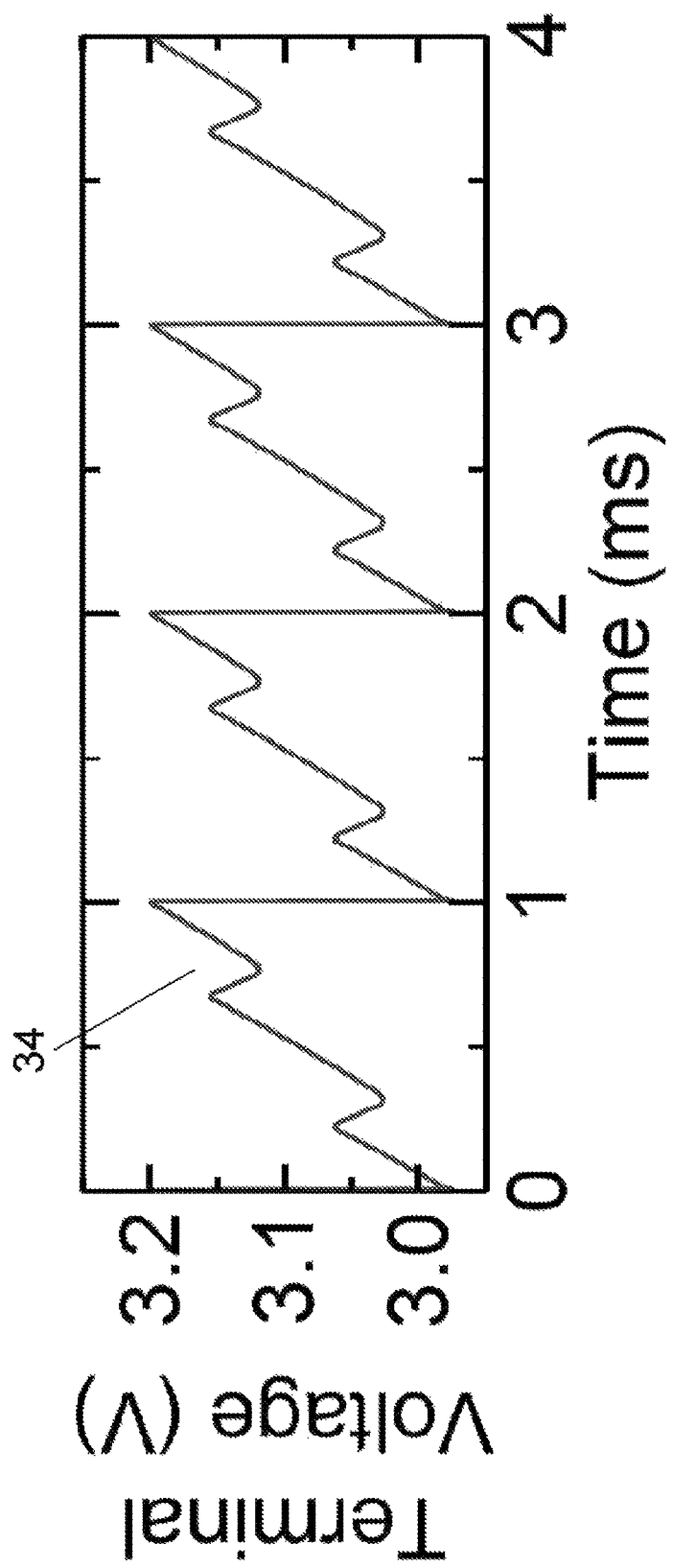
FIG. 2B is a graph corresponding to that of FIG. 2A but of the voltage signal measured across the laser terminals. For illustrative purposes, the magnitude of the self-mixing signal has been increased ten-fold.
Figure 2C:
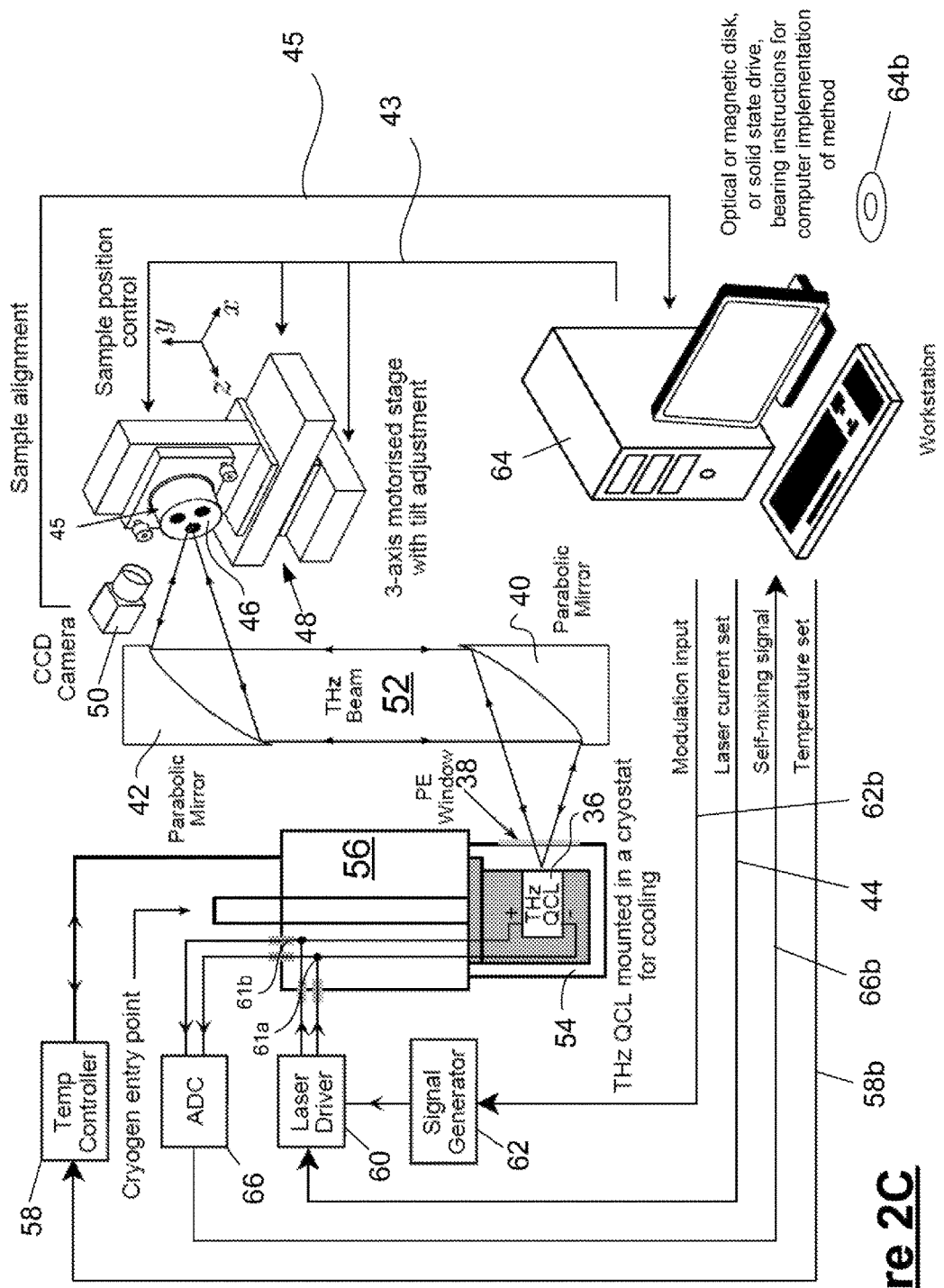
FIG. 2C depicts a system according to a preferred embodiment of the present invention for imaging of a reflective target wherein a QCL is driven by a sawtooth current signal and the QCL terminal voltage variations are acquired using a PC-based data acquisition card (ADC). A pair of parabolic mirrors focuses the beam onto a remote target assembly including a remote target containing materials under test, mounted on a computer-controlled translation stage.

A schematic diagram of the experimental apparatus used is shown in FIG. 2c. The THz QCL 36 (operating at 2.59 THz) consisted of a 11.6-μm-thick GaAs/AlGaAs bound-to-continuum active-region that was processed into a semi-insulating surface-plasmon ridge waveguide with dimensions 1.78 mm×140 μm (see Methods). The QCL was mounted onto the cold finger of a continuous-flow cryostat fitted with a polythene window 38 and operated in cw mode at a heat sink temperature of 15 K. Radiation from the QCL was collimated using a 2 inch diameter, 4 inch focal length off-axis parabolic reflector 40 and focused onto the target using a second identical mirror 42. The total optical path between source and object was 568.2 mm through an ambient (unpurged) atmosphere.

Figure 2D:
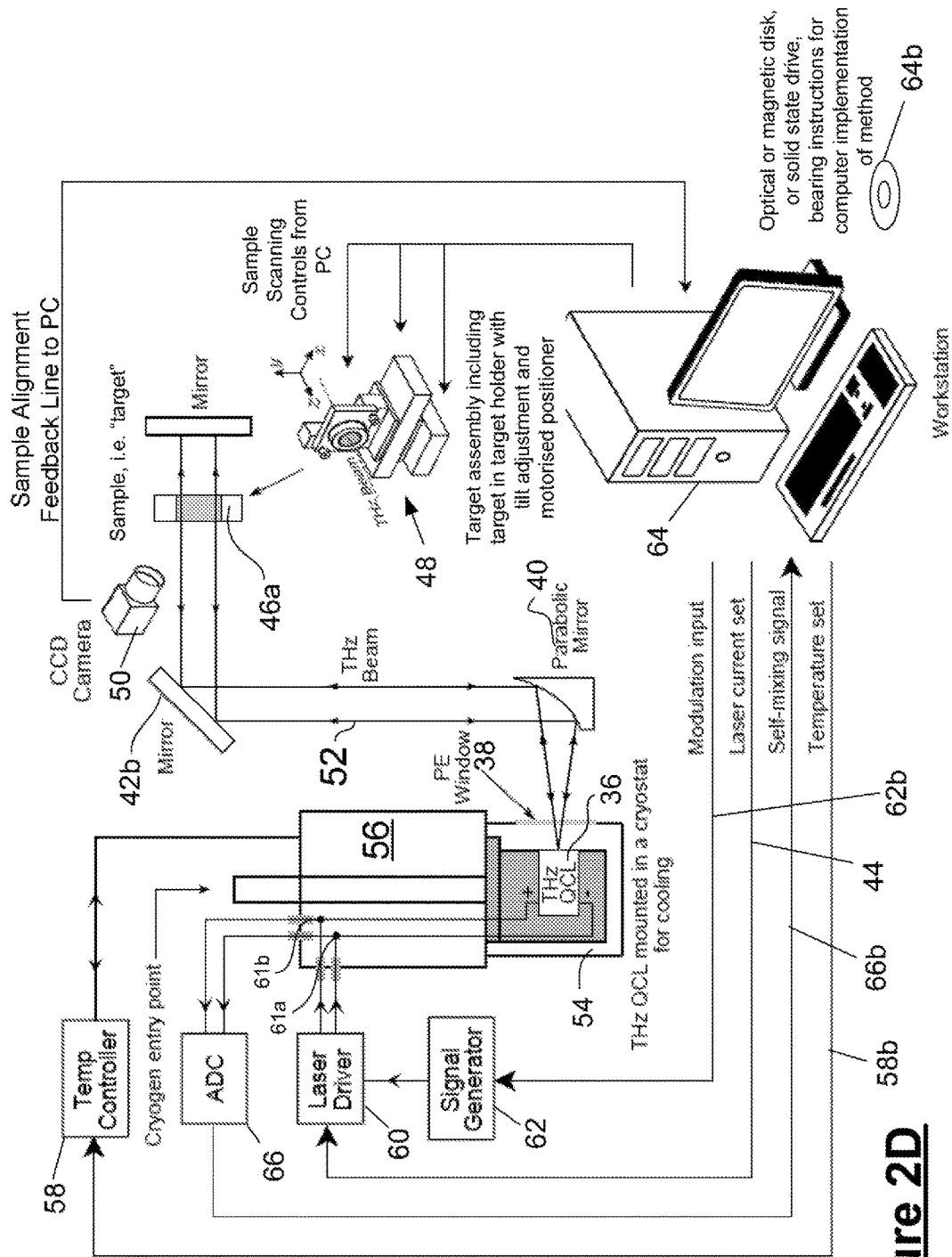
FIG. 2D depicts a version of the system of FIG. 2C adapted for analysis of a light transmissive sample.

In FIGS. 2C and 2D, the modulation input to the signal generator 62 is labeled as 62b. The Self mixing signal sent to computer 64 is labeled as 66b. The temperature setting that is sent to the temperature controller 58 is labeled as 58b. The optical, magnetic or solid state disk bearing instructions for computer 64 to implement the method according to preferred embodiment of the present invention is labeled as 64b.

The laser 36 was driven by a current source in the form of laser driver 60 at $I_{dc}$=0.43 A, slightly above the threshold ($I_{th}$=0.4 A), where the sensitivity to optical feedback is at a maximum. A modulating saw-tooth current signal 32, illustrated in FIG. 2a, having a 50 mA peak-to-peak amplitude was superimposed on the dc current. This leads to a linear frequency sweep of 600 MHz. Owing to optical feedback from the material under test, the self-mixing waveform containing information about the target is embedded in the voltage signal 34 (illustrated in FIG. 2b) that is measured across the laser terminals 61a and 61b and digitized by ADC 66 for delivery to computer 64 and subsequent processing. For image acquisition, the target sample 46, which is supported by target assembly 45, was raster-scanned in two dimensions using a two-axis computer-controllable translation stage 48 (see FIG. 3a for an image of the front surface of the target 46). The translation stage 48 includes actuators that are responsive to control signals on line 43 from the computational device in the form of PC 64. Alignment feedback signals are delivered back to the PC 64 from the translation stage 48 on line 45 to assist the PC in accurately positioning the target. Time domain traces were acquired at each of a plurality of positions, namely at each node of a 181×181 square grid superimposed on the target with spatial resolution of 100 μm. For each spatial pixel of the target, the voltage signal was recorded as the average of 128 time-domain traces.

Therefore the complete set of experimental data contains 181×181 time-domain waveforms, each corresponding to one spatial pixel on the target.

Embodiments of the invention encompass at least two processing procedures. First, a range of high-contrast THz images can be created by processing the self-mixing signals. Second, it is possible to extract absolute values for n and k for any region on the target, provided precise values of n and k are known at two other positions on the target.

Imaging

To obtain high-contrast THz images, the first step is to take each voltage signal and subtract a reference slope, thereby removing the effect of power modulation of the laser; stronger feedback leads to more pronounced departure of the voltage signal from the reference slope.

The effect of transients present around the edges of the modulation period of the laser is removed by using only the central 80% of each self-mixing trace. FIG. 3b shows a two-dimensional representation of the set of time-domain self-mixing signals 74 acquired along the representative horizontal line 70 in FIG. 3a, with the vertical axis showing temporal evolution of the self-mixing signal and the horizontal axis showing its spatial dependence. The shading quantifies the instantaneous amplitude of the self-mixing signal (reference slope already removed). One should bear in mind that due to the coherent nature of the detection scheme the signal strength at a particular point in time cannot be simply related to the reflection coefficient of the target; rather, it is the integral of the absolute value of the signal over time that is proportional to the reflectivity of the target. Further, this quantity is indicative of the strength of the self-mixing signal, with stronger feedback yielding a larger value. In FIG. 3c, this stronger feedback is spatially represented to an observer by the resulting image 73a of the target having a copper-colour end 72 of the pseudocolor range, corresponding to the aluminium part of the target. Weaker feedback regions, corresponding to plastic insets 68 in the aluminium target, are visible as black circles. Due to the strong reflection from aluminium and similar reflectivity of the three plastics at 2.59 THz, contrast between the three plastic insets is not visually discernible in FIG. 3c. However, it is perfectly preserved in the time domain signal, as can be seen from the exemplar time domain traces 76 plotted in FIG. 3e corresponding to each of the three plastic regions.

The amplitude-like codification of self-mixing signal (FIG. 3c) is exploiting just one part of the information embedded in it. Another possible representation relates to the phase, or equivalently the temporal position, of the peaks of the self-mixing signal relative to the edge of the modulating sawtooth signal. Different materials impose different phase-shifts on the incident THz wave according to their complex refractive index, dominated by its imaginary part. This phase-like representation of the effect of the target on the self-mixing signal is shown in the image 73b of the target that is presented in FIG. 3d. Whilst visually this does not show the obvious contrast of the amplitude-like representation, it is interesting to note that these two pieces of information can be likened to the change in the magnitude and the phase of the complex reflectivity, respectively. These two reductions of the information contained in the self-mixing signal are by no means the only ones possible. For instance, by fitting these time-domain traces to the steady-state solution of the Lang and Kobayashi model, one obtains images through plotting the spatial variations in feedback parameter C.

Materials Analysis:

While the signal processing for creating images in FIG. 3(c,d) is quite straight forward, the procedure for extracting optical constants of materials under test requires multiple steps, including fitting. As discussed earlier, the target used in this study contains three plastic materials 68 embedded in an aluminium holder 72 (FIG. 3a). For this procedure, it is assumed that the complex refractive indices of two of these materials are known in order to determine the third. To establish the self-consistency of the scheme, this approach is adopted for each of the three materials in turn. In order to exclude the effects of the boundary between the materials and the aluminium holder measurements are used from inside the circles superimposed on the photograph in FIG. 3a to determine the complex refractive index of each material under test. Referring to FIG. 1a, the total phase delay in the external cavity 13 can be decomposed into the transmission phase delay arising from the round-trip 15 through the cavity and the phase change on reflection from the target, which is material dependent. The second order effect of the linear current sweep is a linear chirp of the lasing frequency (600 MHz), leading to a linear dependence of transmission phase with time. Therefore the external phase delay (interferometric phase) $\varphi$ over one frequency modulation period T as a function of time is of the form $$\varphi(t) = \varphi_0 + \frac{\phi_\Delta}{T} t - \theta_R \quad (1)$$

where $\varphi_0$ is the round-trip transmission phase delay in the external cavity at the start of the frequency sweep, $\Phi_\Delta$ is the interferometric phase deviation caused by the current (frequency) sweep, and $\theta_R$ the phase change on reflection from the material under test. Clearly, $\varphi$ is a function of the instantaneous laser frequency, which depends on the level of feedback in the laser system.

According to the Lang and Kobayashi model for a semiconductor laser under optical feedback in a steady state the laser frequency satisfies the phase condition (sometimes called the excess phase equation)

$$\varphi_s - \varphi_{FB} = C \sin(\varphi_{FB} + \arctan \alpha) \quad (2)$$

where $\varphi_{FB}$ represents the total external round-trip phase at the perturbed laser frequency, $\varphi_s$ represents the total external round-trip phase at the solitary laser frequency, C is the feedback parameter that depends on the amount of light reflected back into the laser cavity, and $\alpha$ is the line width enhancement factor. Solutions to equation (2) are not possible in closed form and therefore require numerical solution. The interferometric phase change is directly observable through the change in emitted optical power, or equivalently through the change in voltage across the laser terminals, as is used in the presently described preferred embodiment of the invention. The self-mixing signal embedded in the modulated voltage signal is related to the phase change through $$V = V_0 + \beta \cos(\varphi_{FB}) \quad (3)$$

where V is the voltage waveform obtained after the removal of the common slope, $V_0$ is a dc component of this signal (corresponding to a material-dependent voltage offset from the reference slope), and $\beta$ is the modulation index. Note that, for the modulation scheme used here, V is a function of time through its dependence on the interferometric phase $\varphi_{FB}$.

Thus a parametric model is obtained, based directly on the steady state solution to the Lang and Kobayashi model, that describes well the set of experimentally acquired time domain traces. Equations (1)-(3) form a model with six key parameters, namely C, $\alpha$, $\theta_R$, $\Phi_\Delta$, $V_0$ and $\beta$. The information about the complex refractive index to be extracted is encoded mainly in C, $\alpha$, and $\theta_R$. To extract these parameters, fit the model to data in the least-squares sense, for each spatial pixel of the target. This provides a set of parameter values for each pixel inside the coloured circles in FIG. 3a.

If n and k of two of the materials are known, it is then possible to exploit their relationship to the parametric model and thereby derive n and k of the third material (the material under test—see Methods). Results for six materials under test obtained from two different targets are tabulated in Table 1 and compared against reference values from the literature.

TABLE 1

Results for six materials under test obtained from two different targets compared against reference values from the literature.

| | Estimated n | Reference n | Estimated k | Reference k |
|---|---|---|---|---|
| POM | 1.65 | 1.66 | 0.011 | 0.012 |
| PVC | 1.66 | 1.66 | 0.063 | 0.062 |
| PA6 | 1.66 | 1.67 | 0.11 | 0.11 |
| PC | 1.62 | 1.62 | 0.011 | 0.011 |
| HDPE Black | 1.58 | 1.58 | 0.019 | 0.018 |
| HDPE | 1.54 | 1.54 | 0.0022 | 0.0020 |

In summary, a preferred embodiment of the present invention provides a feedback interferometric approach to the optical analysis of materials at THz frequencies. Using this simple, robust approach, both intensity- and phase-like images of materials are acquired concurrently. This technique enables the user to interrogate regions of the target and extract precise values for refractive index and absorption coefficient within these defined areas. Such characterisation of the optical properties of substances at THz frequencies enhance the identification and discrimination in the materials science.

Methods

Laser Fabrication and Operation:

The THz QCL heterostructure was based on a GaAs/AlGaAsbound-to-continuum active region design operating at 2.59 THz. The wafer was grown on a semi-insulating GaAs substrate by molecular beam epitaxy, with an active region thickness of 11.6 μm, consisting of 90 repetitions of the gain medium. The active region stack was sandwiched between doped upper 80-nm-thick ($n=5\times10^{18}$ cm$^{-3}$) and lower 700-nm-thick ($n=2\times10^{18}$ cm$^{-3}$) GaAs contact layers. The wafer was processed into a surface plasmon ridge waveguide using optical lithography and wet chemical etching with confinement of the waveguide mode being ensured by the lower doped layer. Optical lithography was used for defining ohmic contacts, the thicknesses of the Au/Ge/Ni bottom and top contacts being 200 nm and 100 nm, respectively. The thickness of the Ti/Au overlayer was 20 nm/200 nm and the substrate was thinned to a thickness of ~200 μm·A 140 μm ridge width was used and the cleaved device facets were left uncoated.

The device was mounted on a copper bar using indium foil to provide thermal contact, and was then wire bonded. In all experiments, the laser was operated using a constant current source at $I_{dc}$=0.43 A. A modulating saw-tooth current signal (50 mA peak-to-peak amplitude) was superimposed on the dc current, leading to a linear sweep of the lasing frequency of 600 MHz.

System and Measurement Calibration:

The refractive index n and the extinction coefficient k of the target directly affect the self-mixing voltage in our model through the phase-shift on reflection $\theta_R$. Moreover, the reflectance of the target R is directly linked to the model parameters C and α through the definition of the feedback parameter C, known in the literature as:

$$\sqrt{R} \propto \frac{C}{\sqrt{1+\alpha^2}} \quad (4)$$

To account for external reflections other than that from the target (including reflections from the cryostat shield and the window), $\sqrt{R}$ is written as $$\sqrt{R^M} = a_R + b_R \sqrt{R^A} \quad (5)$$

where $\sqrt{R^A}$ is the actual reflectance of the material under test, $a_R$ and $b_R$ are unknown parameters to be determined, and $$\sqrt{R^M} = \frac{C}{\sqrt{1+\alpha^2}}$$

is representative of the material's measured, but uncalibrated reflectance.

Along similar lines, to account for systematic phase changes, $\theta_R$ is expressed as $$\theta_R^M = a_\theta + b_\theta \theta_R^A \quad (6)$$

where $\theta_R^A$ is the actual phase shift on reflection, $a_\theta$ and $b_\theta$ are unknown parameters to be determined, and $\theta_R^A$ is representative of the uncalibrated phase shift on reflection.

Equations (5) and (6) contain four unknown parameters, $a_R$, $b_R$, $a_\theta$ and $b_\theta$, which can be determined from two measurements on materials with known ($\sqrt{R^A}$, $\theta_R^A$) values, which can be viewed as a set of four linear equations with four unknowns. Denoting the calibration pairs of measured and actual reflectances and phase-shifts for the two standards as $(R_1^M, R_1^A)(\theta_{R,1}^M, \theta_{R,1}^A)$ and $(R_2^M, R_2^A)(\theta_{R,2}^M, \theta_{R,2}^A)$ respectively, the set of our linear equations are $$\sqrt{R_1^M} = a_R + b_R \sqrt{R_1^A} \quad (7a)$$

$$\sqrt{R_2^M} = a_R + b_R \sqrt{R_2^A} \quad (7b)$$

$$\theta_{R,1}^M = a_\theta + b_\theta \theta_{R,1}^A \quad (7c)$$

$$\theta_{R,2}^M = a_\theta + b_\theta \theta_{R,2}^A \quad (7d)$$

The solution of this system of equations is straightforward and provides values for $a_R$, $b_R$, $a_\theta$ and $b_\theta$. Once these values have been obtained using (5) and (6) actual values for $\theta_R^A$ and $R^A$ for the material under test can be readily calculated. The relationship between (R, $\theta_R$) and (n, k) is given through the pair of relations $$n = \frac{1-R}{1+R-2\sqrt{R}\cos(\theta_R)} \quad (8a)$$

$$n = \frac{2\sqrt{R}\sin(\theta_R)}{1+R-2\sqrt{R}\cos(\theta_R)} \quad (8b)$$

Figure 3A:
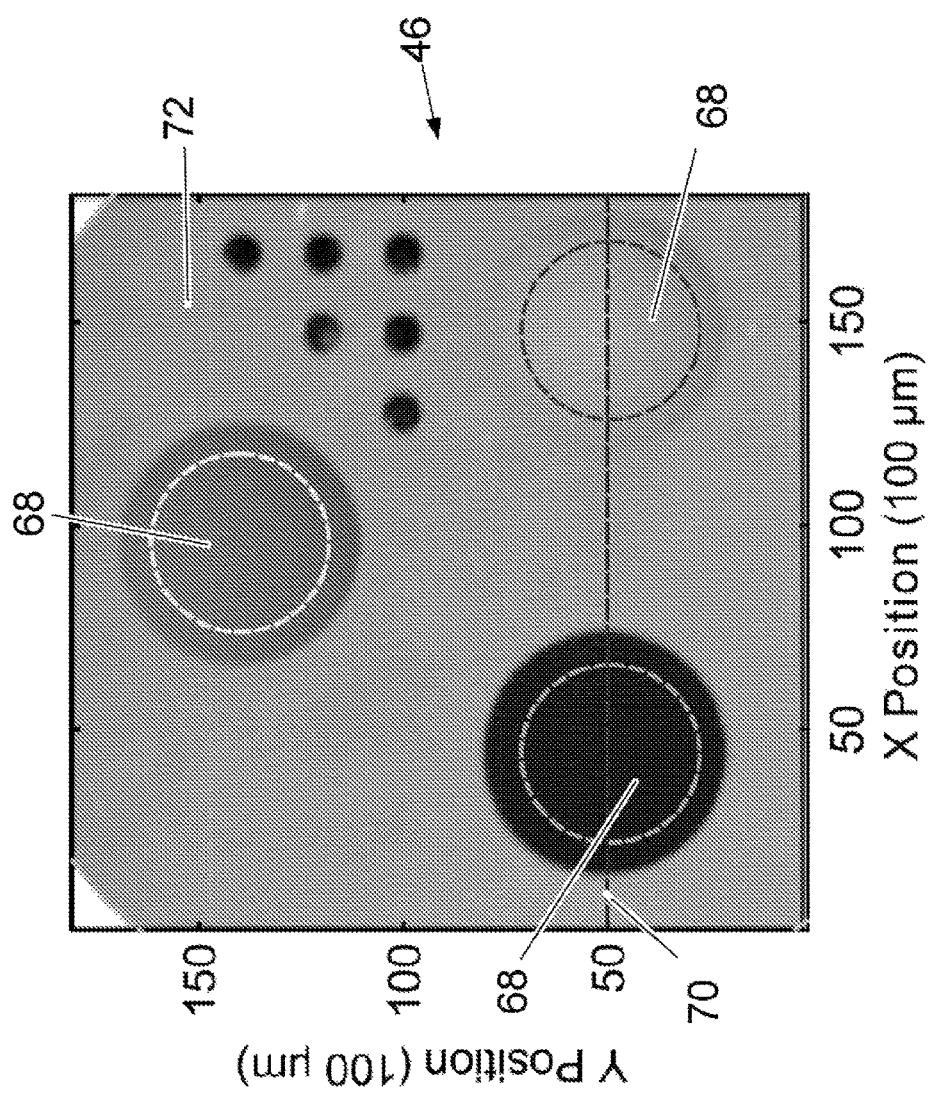
FIG. 3A is a photograph of the front surface of a target of FIG. 2C discussed during an explanation of the use of the system. The three circular regions are materials under test embedded in an aluminium holder, namely PA6 PVC and POM.
Figure 3B:
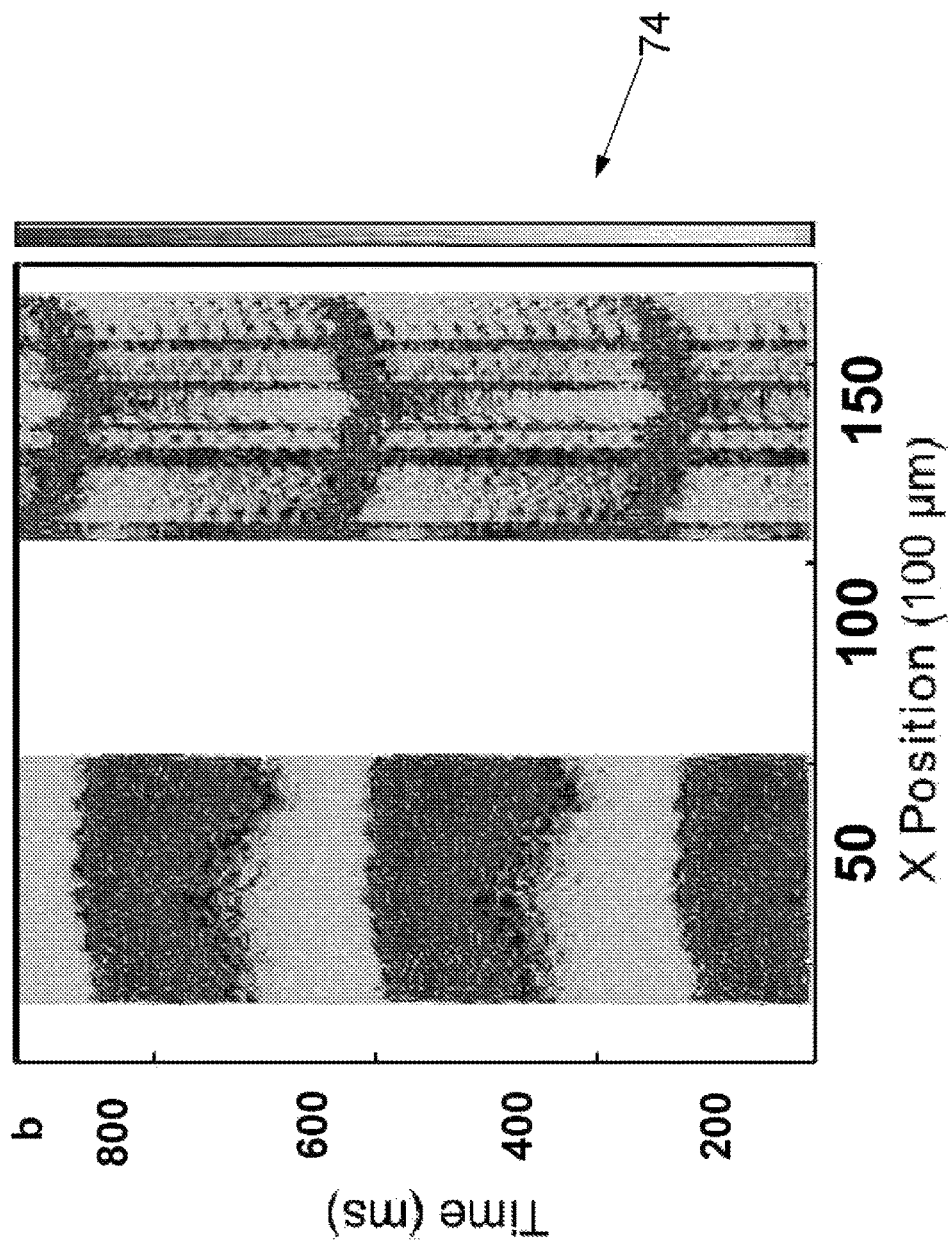
FIG. 3B is a two-dimensional representation of time domain self-mixing signals acquired along representative line 70 in FIG. 3A, each showing three fringes. The vertical axis represents the temporal evolution of the signal whilst horizontal axis shows their spatial dependence.
Figure 3C:
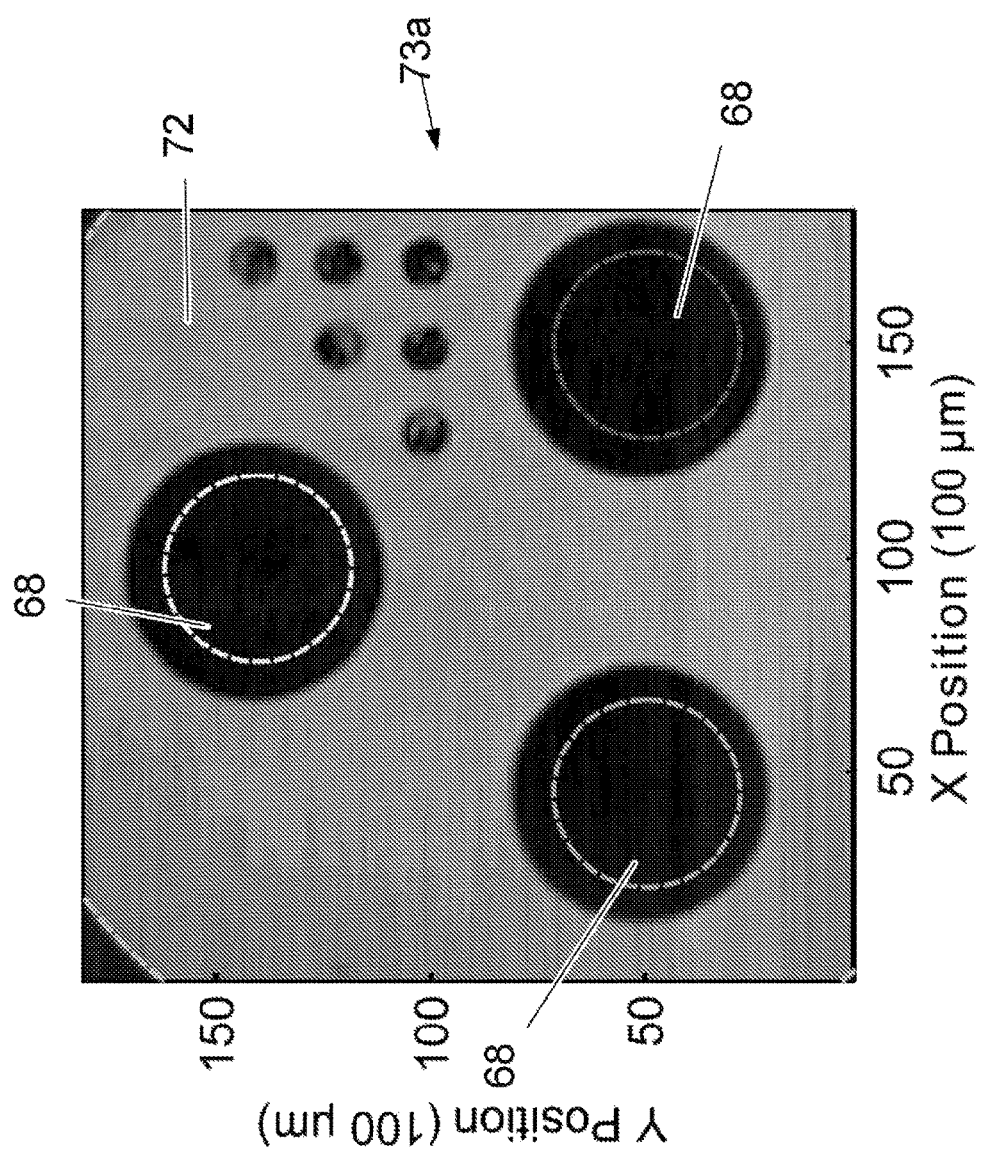
FIG. 3C shows an amplitude-like image wherein a pseudo-colour plot represents the effective aggregate difference between the time domain trace relative to the reference slope.
Figure 3D:
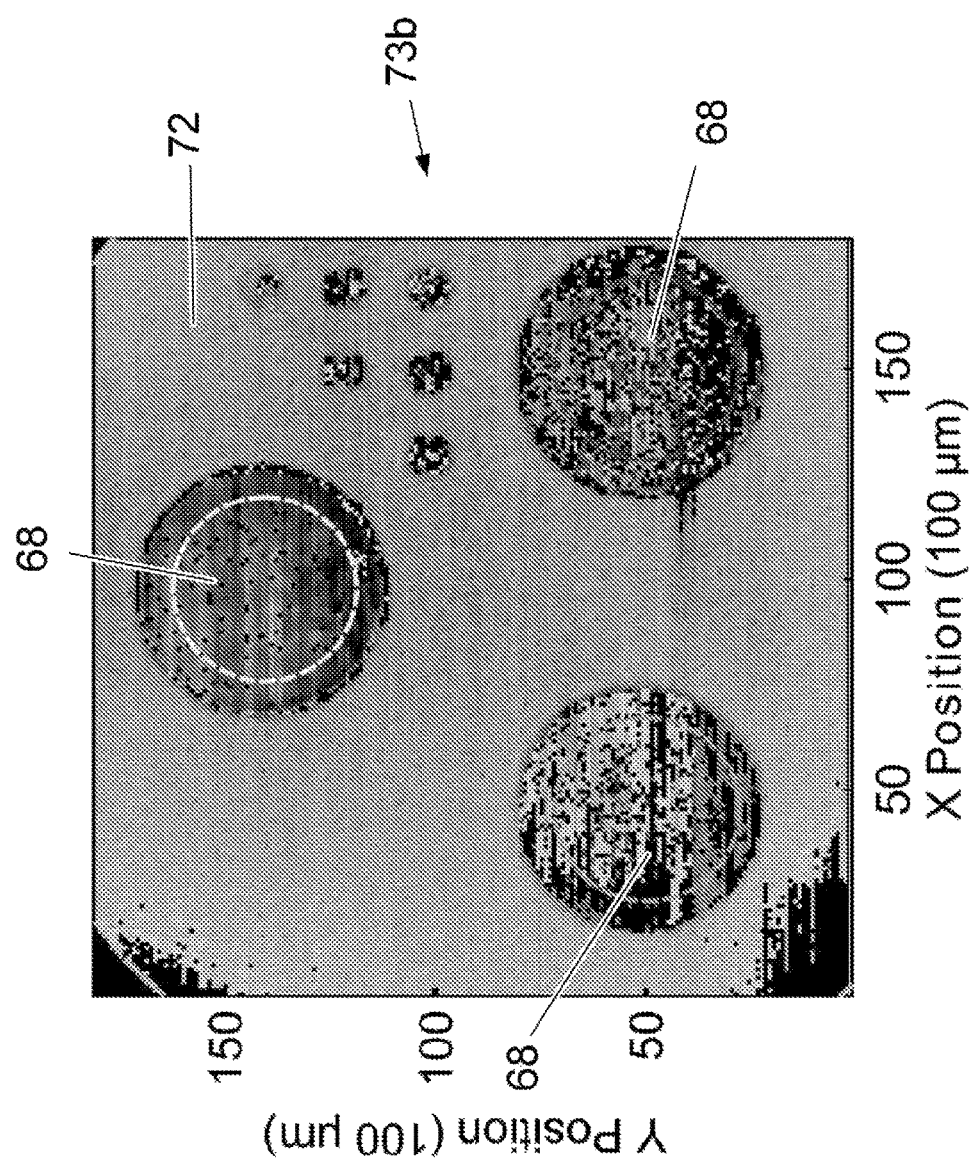
FIG. 3D shows a phase-like image wherein a pseudo-colour plot is based on the temporal location of the representative peak of the self-mixing signal relative to the edge of the modulation waveform.
Figure 3E:
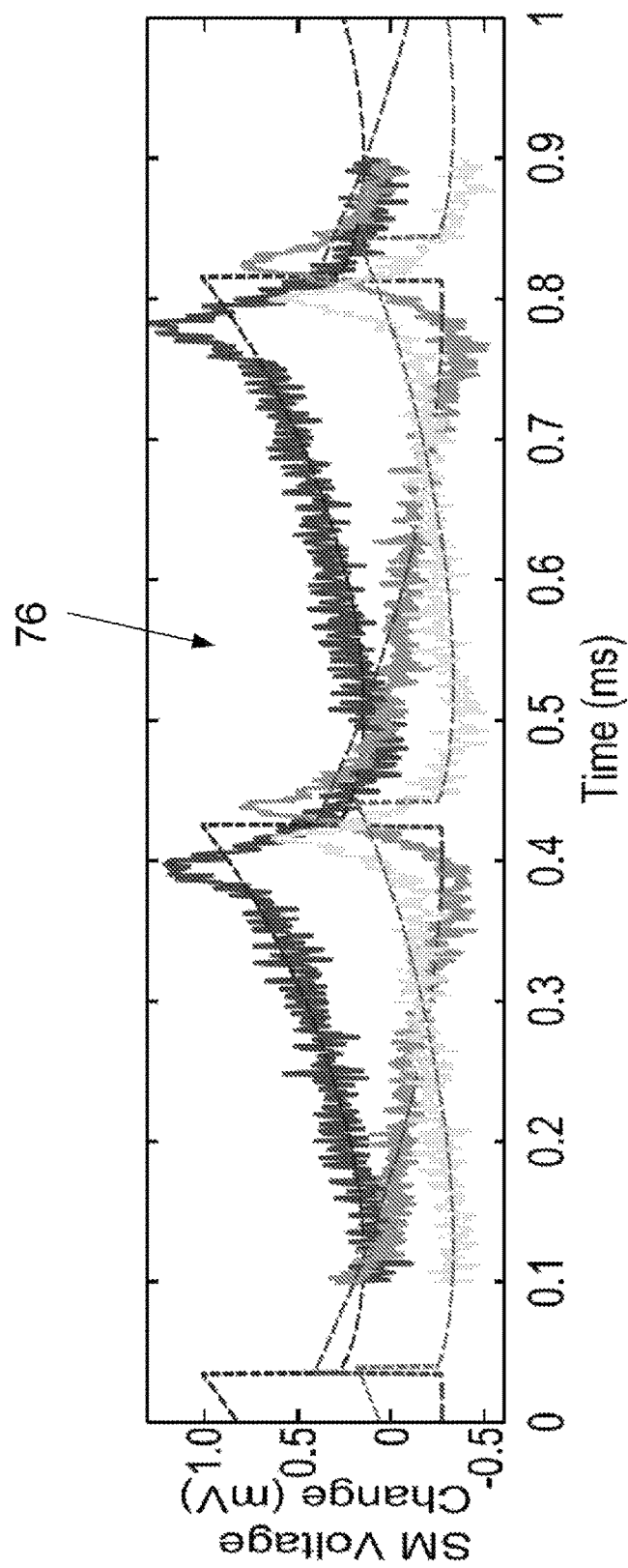
FIG. 3E depicts a representative time domain waveforms for one spatial pixel on the target per material (solid lines) with corresponding model fits (broken lines). The common reference slope has been removed.

This procedure is applied to the three materials embedded in the target (see FIG. 3a). Values from the literature for optical constants for two of the materials were used, treating them as standards in this procedure to obtain values for the unknowns $a_R$, $b_R$, $a_\theta$ and $b_\theta$.

USE FOR THE INVENTION

An example of the use of a preferred embodiment of the invention will now be provided with reference to FIG. 2C. It will be realised that the steps outlined below may also be applied in an entirely analogous manner to the transmission sample setup of FIG. 2D.

1. Setting up sample
   a. Put prepared sample 46, i.e. the target, to be imaged/analysed in sample holder on the 3-axis motorised stage 48.
   b. Adjust position (tilt and XYZ) using the CCD camera 50 to align sample surface to the focal plane of the THz beam 52.
2. Preparing THz QCL for operation
   a. Connect vacuum pump to cryostat 54.
   b. Evacuate vacuum chamber of cryostat (using vacuum pump).
   c. Disconnect vacuum pump.
   d. Insert cryogen transfer line into the Dewar 56 and cryostat allowing cryogen to flow into cryostat and begin cooling the laser.
   e. Turn on temperature controller 58 and adjust the set point to 15K (optimal operating temperature for this particular THz QCL).
   f. Wait until cryostat is stable at 15K.
   g. Turn on Laser driver 60 at DC current bias (typically 0.43 A (again for this particular THz QCL)).
   h. Setup signal generator 62 to generate a modulating sawtooth wave (typical 1 V at 1 KHz) and feed into the laser driver (1 V modulation input=50 mA output to laser. (So laser drive current is 0.43 to 0.48 A in a ramp))
   i. Enable output of signal generator.
   j. Wait for laser temperature to stabilise.
   k. The THz QCL is now ready and emitting the measurement beam
3. Measure Target
   a. Setup XY raster scan of target area (X-Y translation (typ. 18 mm×18 mm), step size (typ. 100 μm) controlled via computer 64) to scan through a plurality of positions. Initial position is centre point of scan.
   b. Start Scan
      i. Motorised stage moves to a pixel position
      ii. Take several measurements (via the ADC 66) of the terminal voltage of the THz QCL (typical 128 Averages, of 1K of samples at 1M samples/s).

iii. Save average sample to the workstation.
iv. Translate sample to next imaging pixel & repeat (i-iii).
c. When scan finished move back to the starting position (centre of scanned area).
4. Shut down measurement
a. Turn off Laser driver and signal generator.
b. Shut off cryogen flow and remove cryogen transfer line from the cryostat.
c. Turn off temperature controller.
5. Processing Data
a. Waveforms are processed using the workstation.
b. Prepare waveforms for fitting
  i. Remove the power ramp (average ramp of signals)
  ii. Trim ends (~100 data points) to avoid edge transients.
  iii. Optionally adjust for known tilt of the sample surface.
c. For each spatial pixel, fit excess phase SM model to data (typically in least-squares sense) and extract $\sqrt{R^M}$ (amplitude reflectivity proxy) & $\theta_R^M$ (phase proxy) as functions of fitted SM model parameters.
d. Images showing the relative change in (for example) reflectivity proxy, phase proxy, or SM model parameters across the surface of the target can then be produced.
e. For absolute parameter extraction
  i. At least two known materials have been scanned (at the same time) in addition to the unknown sample.
  ii. All material samples lie on the same known surface (typically a plane).
  iii. System error coefficients are calibrated based on measured and known pairs.
  iv. Material parameters of the unknown sample can then be estimated using measured values and known system error coefficients.

POTENTIAL APPLICATIONS FOR THE INVENTION

Detection of Skin Malignancy In Vivo—

Work using time domain spectroscopy based imaging of skin tissue samples has shown the ability to discriminate basal cell carcinoma (BCC) from surrounding healthy tissue. In a series of 15 excised cases, THz contrast always exceeded visible contrast upon which the conventional imaging diagnosis is made. Clearly, the molecular composition of cancerous tissue will differ, giving rise to differing vibrational modes within the THz range, and thereby a contrast in complex permittivity. The orientation of microstructure (i.e. fiber orientation, cellular arrangement) is also perturbed in tumour tissue, which can be detected through measurement of the interaction of THz irradiation. The exact nature of these responses of various cancer types to THz interrogation are of value as the basis for discrimination tools for non-invasive in-vivo THz imaging of human skin.

Discrimination of disease states in biological specimens and tissue biopsy samples using THz based image contrast and spectroscopic data is also possible using the techniques described herein. Prepared specimens of fluids, or solid tissue can be interrogated for differences in THz characteristics based on the complex permittivity information gained. Changes in the chemical constitution and structural changes associated with acquired disease will be the primary sources of discrimination between normal and pathological specimens. The differences observed may not necessarily be present when examined at frequencies outside the THz band. This application will however require ex vivo specimens in contrast to the above application, which is aimed at in vivo diagnosis.

Pharmaceuticals

Analysis and monitoring of pharmaceutical materials in production processes is possible using the techniques described herein. The characterisation and control of all possible polymorphic forms of pharmaceutical ingredients (e.g. in tablet formulations) is a key factor in the pharmaceutical industry. Experiments have demonstrated that THz spectroscopic techniques can distinguish between different polymorphic forms of pharmaceutical solids (for example carbamazepine, enalapril maleate, sulfathiazole amongst others), by virtue of structural differences (and hence differences in the intermolecular vibrations) in these polymorphs. Thus, prepared pharmaceutical samples can be interrogated for differences in THz characteristics based on the complex permittivity information gained. This application has the potential for production-line monitoring, including monitoring through capsules. Alternative techniques for monitoring such structural differences, such as X-ray powder diffraction, are considerably slower. Furthermore, near- and mid-infrared spectroscopies are generally less sensitive to polymorphic changes.

Security

Embodiments of the invention may be used to detect explosives (e.g. RDX, PETN, TNT, HMX), weapons and the like and so may assist in postal and packaging inspections.

Detection/sensing of crystalline explosives (for example RDX, PETN, TNT, HMX) and illicit drugs (for example cocaine, methamphetamine, heroin) is possible using the techniques described herein. Experiments have demonstrated that such materials can be readily identified using THz spectroscopic techniques. Thus, prepared explosive/drug samples can be interrogated for differences in THz characteristics based on the complex permittivity information gained. THz radiation also penetrates many packaging materials, enabling identification of concealed illicit compounds (for example in postal inspection).

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A method for investigating a target comprising the steps of:
   directing a first beam of radiation, from a laser radiation source in a laser cavity, at the target to thereby produce a second beam of laser radiation by interaction of the first beam with the target,
   directing the second beam of laser radiation into the laser cavity wherein self-mixing of the first and second beams occurs within the laser cavity;
   varying a parameter affecting the interaction of the first beam with the target;
   detecting a signal arising from the self-mixing; and
   processing the signal to thereby determine phase and amplitude changes associated with material properties of the target to derive a refractive index (n) and an extinction coefficient (k) of the target,
   wherein the method measures both real and imaginary parts concurrently.

2. A method according to claim 1, wherein the laser is arranged to operate in the terahertz (THz) band.

3. A method according to claim 1, wherein the laser comprises a quantum cascade laser (QCL).

4. A method according to claim 1, wherein the step of detecting the signal involves monitoring an electrical signal across terminals of the laser.

5. A method according to claim 1, wherein the step of varying a parameter includes applying a modulation to a current for driving the laser.

6. A method according to claim 5, wherein the modulation comprises a continuous wave frequency modulation of the laser beam frequency.

7. A method according to claim 1, wherein the step of processing the signal includes detecting a phase shift of a waveform of the signal associated with a phase shift imparted by the interaction of the first beam with the target.

8. A method according to claim 7, wherein the step of processing the signal further includes detecting a change of the waveform of the signal associated with an attenuation imparted by the interaction of the first beam with the target.

9. A method according to claim 1, wherein the step of varying the parameter may comprise moving the target toward or away from a source of the first beam of laser radiation.

10. A method according to claim 1, including causing the first beam of laser radiation to interact with a portion of the target having known properties.

11. A method according to claim 10, including applying known values of n and k of two materials from said portion of the target having known values to thereby derive n and k of a third material of the target, being a material under test.

12. A method according to claim 11 including fitting a mathematical model of said laser self-mixing to data for each of a number of positions of the target to obtain a set of parameter values for each of the positions.

13. A method according to claim 1, including mechanically scanning the target by moving the target relative to the laser through a plurality of positions to thereby sense variations in the properties of the target as a function of location thereof.

14. A method according to claim 13, including processing the sensed variations in the properties of the target to produce an image of the target.

15. A method according to claim 14, including making measurements of variations in the signal at each of a number of positions during the mechanical scanning.

16. A method according to claim 15 including removing effects due to power modulation of the laser from each of said measurements.

17. A method according to claim 15 including processing only a portion of each modulation period of the signal at each scanning position to avoid the effect of transients at edges of a modulation period of the laser, wherein the said portion of the modulation period excludes the edges.

18. A method according to claim 15 including determining a reflection coefficient of the target at each position.

19. A method according to claim 18 wherein the step of determining the reflection coefficient is based on an integral of an absolute value of the signal over time.

20. A method according to claim 19 including producing an image from the target by fitting time domain traces of the signal to a mathematical model of said laser self-mixing to thereby calculate variations in a feedback parameter of the model wherein the image is generated by plotting the feedback parameter for each of a number of the positions.

21. A system for investigating a target comprising:
   a laser;
   a target assembly arranged to receive an incident beam from the laser and return a beam back to the laser after interaction of the incident beam with a target of said assembly;
   a data acquisition assembly responsive to electrical terminals of the laser; and
   a computational device responsive to the data acquisition assembly, wherein the computational device is programmed to determine phase and amplitude changes associated with the target and imparted on to the beam returned back to the laser after the interaction,
   wherein the system measures both real and imaginary parts concurrently.

22. A system according to claim 21 wherein the laser is under control of the computational device for operation of the laser and variation of its operating parameters.

23. A system according to claim 21 including a translation assembly arranged to impart a relative motion between the laser and the target.

24. A system according to claim 23, wherein the translation assembly includes one or more actuators under control of the computational device wherein the computational device is programmed to operate the translation assembly for data acquisition at each of a number of positions of the target.

25. A computer software product comprising a non-transitory machine readable media configured to provide instructions for an electronic processor to:
   operate a laser to direct a laser beam at a target assembly;
   acquire electrical data being a function of self-mixing of the laser beam with a reflection thereof subsequent to interaction with the target assembly; and
   determine phase and amplitude changing properties of a target portion of the target assembly on the basis of the acquired electrical data,
   wherein the product measures both real and imaginary parts concurrently.

* * * * *